(12) United States Patent
Tajima et al.

(10) Patent No.: US 6,618,927 B2
(45) Date of Patent: Sep. 16, 2003

(54) METHOD FOR MANUFACTURING A GAS SENSOR

(75) Inventors: Hideyuki Tajima, Oobu (JP); Norihiko Nakano, Anjo (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 09/885,022

(22) Filed: Jun. 21, 2001

(65) Prior Publication Data

US 2002/0000033 A1 Jan. 3, 2002

(30) Foreign Application Priority Data

Jun. 30, 2000 (JP) .......................................... 2000-197995
Mar. 29, 2001 (JP) .......................................... 2001-096592

(51) Int. Cl.⁷ ................................................ G01R 3/00
(52) U.S. Cl. .................... 29/595; 29/90.7; 29/DIG. 36; 72/53; 73/11.03
(58) Field of Search ................. 29/469.5, 594, 29/595, 609.1, DIG. 87, DIG. 36, DIG. 41, DIG. 43, 90.7; 72/53, 347, 349; 73/11.02, 273; 451/38, 39, 40

(56) References Cited

U.S. PATENT DOCUMENTS

| | | | | |
|---|---|---|---|---|
| 540,314 A | * | 6/1895 | Howell ................ | 29/DIG. 43 |
| 3,485,073 A | * | 12/1969 | Burney ................ | 72/53 |
| 3,654,786 A | * | 4/1972 | Koenecke et al. .... | 72/53 |
| 5,293,320 A | * | 3/1994 | Thompson et al. ... | 72/53 |
| 5,817,920 A | * | 10/1998 | Kuisell et al. ....... | 73/23.31 |
| 5,874,663 A | * | 2/1999 | Fukaya et al. ....... | 73/23.32 |
| 5,874,664 A | | 2/1999 | Watanabe et al. .... | 73/116 |
| 6,038,900 A | * | 3/2000 | Miyasaka ............. | 72/53 |

FOREIGN PATENT DOCUMENTS

| | | | |
|---|---|---|---|
| JP | 53124115 | * | 10/1978 |
| JP | 4-246123 | | 9/1992 |
| JP | 9-210953 | | 8/1997 |

* cited by examiner

Primary Examiner—Peter Vo
Assistant Examiner—Donghai Nguyen
(74) Attorney, Agent, or Firm—Nixon & Vanderhye PC (57) ABSTRACT

A sensing element, disposed in a housing, has a gas contact portion exposed to a measured gas. A protective cover extends from a distal end of the housing so as to surround the gas contact portion of the sensing element. A first metallic cover surrounds signal output terminals and leads connected to the sensing element. In manufacturing the first metallic cover, a shot blasting is applied to a surface of a semi-finished product of the first metallic cover.

20 Claims, 9 Drawing Sheets

METHOD FOR MANUFACTURING A GAS SENSOR

BACKGROUND OF THE INVENTION

The present invention relates to a gas sensor installed in an exhaust system of an automotive internal combustion engine to detect an oxygen concentration in the exhaust gas, or an air-fuel ratio or the like.

In general, freeze proofing agent or other salt forms a corrosive environment against a metallic cover of of a gas sensor installed in an automotive vehicle. An internal stress remaining in the metallic cover causes a tensile stress triggering a stress corrosion cracking.

To eliminate the stress corrosion cracking, a conventional press shaping work was performed carefully little by little so as not to leave a residual stress in the processed metallic cover. However, this conventional method increases the total number of processes and time for the press shaping work with increased costs, and is not effective to completely remove the residual stress.

According to another conventional method, a thermal treatment is applied to a processed metallic cover after being shaped into a predetermined shape. However, this conventional method may deteriorate mechanical properties of the metallic cover and will not assure a sufficient strength when this metallic cover is caulked with other member.

SUMMARY OF THE INVENTION

To solve the above-described problems, an object of the present invention is to provide a manufacturing method of a gas sensor which is capable of easily improving the stress corrosion cracking durability of a metallic cover.

In order to accomplish the above and other related objects, the present invention provides a method for manufacturing a gas sensor comprising a sensing element having a gas contact portion exposed to a measured gas, a housing holding the sensing element, a protective cover extending from a distal end of the housing and surrounding the gas contact portion of the sensing element, and a first metallic cover covering signal output terminals and leads connected to the sensing element. The manufacturing method of the present invention comprises a step of forming a semi-finished product of the first metallic cover, and a step of applying a shot blasting to a surface of the semi-finished product of the first metallic cover.

The manufacturing method of the present invention is characterized in that the shot blasting is applied to the surface of the semi-finished product of the first metallic cover.

The shot blasting is generally referred to as a surface processing technique according to which small hard balls, e.g., steel balls, steel wire chips, glass beads or the like, are continuously blown to a surface of a metallic member through a nozzle under pressurized air or by using a turbine wheel or by using other equivalent means.

According to the manufacturing method of the present invention, the first metallic cover is subjected to the shot blast processing after being configured into a predetermined shape. Hence, it becomes possible to reduce the surficial residual tensile stress while maintaining the mechanical properties of the first metallic cover obtained through the press shaping work.

More specifically, when the shot blast processing is applied to the surface of the first metallic cover, a residual compression stress remains in a surficial layer of the first metallic cover due to collision of small balls. The residual compression stress thus given to the surface of the first metallic cover completely cancels or greatly reduces the residual tensile force caused during the press shaping processes of the first metallic cover.

It is technically possible to restrict the shot blasting to only the surficial layer so that no influence of the shot blasting is given to the inner layer of the first metallic cover. Accordingly, the first metallic cover can maintain improved mechanical properties, such as tensile strength, obtained through the press shaping work.

In this manner, applying the shot blast processing to the surface of the first metallic cover makes it possible to reduce the residual tensile stress and improve the stress corrosion cracking durability. Thus, it becomes possible to optimize the press shaping processes so as to give excellent mechanical properties to the first metallic cover.

The manufacturing method of the present invention can greatly reduce the residual tensile stress remaining in the surficial layer of the first metallic cover due to application of the shot blast processing. Thus, the stress corrosion cracking durability can be surely improved.

Furthermore, according to the present invention, it is preferable that the semi-finished product of the first metallic cover is configured into a predetermined shape having a larger-diameter portion positioned near the housing and a smaller-diameter portion positioned far from the housing before applying the shot blasting to said first metallic cover.

Especially, forming the larger-diameter portion positioned near the housing and the smaller-diameter portion positioned far from the housing realizes a compact metallic cover preferably applicable to a gas sensor.

Applying the shot blast processing to the thus shaped metallic cover surely reduces the residual tensile stress and improves the stress corrosion cracking durability.

Furthermore, according to the present invention, it is preferable that the smaller-diameter portion has a hardness higher than that of the larger-diameter portion when the semi-finished product of the first metallic cover is formed.

This arrangement provides a sufficient strength to the first metallic cover when the smaller-diameter portion serves as an inner tube of a double pipe arrangement.

Furthermore, according to the present invention, it is preferable that the semi-finished product of the first metallic cover is formed through the steps of configuring a plate or tubular material into a predetermined shape having the larger-diameter portion, subjecting the shaped material to a thermal treatment, and reshaping part of the thermally treated material to form the smaller-diameter portion.

Adopting these steps makes it easy to differentiate the hardness of the smaller-diameter portion from that of the larger-diameter portion.

Furthermore, according to the present invention, it is preferable that the manufacturing method further comprises a step of overlapping a second metallic cover on an outer surface of the smaller-diameter portion of the first metallic cover, and a step of caulking overlapped portions of the second metallic cover and the smaller-diameter portion of the first metallic cover.

Adopting these steps makes it possible for the first metallic cover to maintain improved mechanical properties obtained through the press shaping work even after the shot blast processing. Thus, it becomes possible to maintain the caulked portion in an optimized condition.

Furthermore, according to the present invention, it is preferable that the manufacturing method further comprises a step of applying a shot blasting to a surface of the second metallic cover beforehand.

Adopting this step surely reduces the residual tensile stress of the second metallic cover, thereby improving the stress corrosion cracking durability of the second metallic cover.

Furthermore, according to the present invention, it is preferable that the manufacturing method further comprises a step of overlapping the larger-diameter portion of the first metallic cover on an outer surface of a third metallic cover at one end thereof after applying the shot blasting to the first metallic cover, while connecting the other end of the third metallic cover to the housing, and a step of caulking overlapped portions of the third metallic cover and the larger-diameter portion of the first metallic cover.

Adopting these steps makes it possible for the first metallic cover to maintain improved mechanical properties obtained through the press shaping work even after the shot blast processing. Thus, it becomes possible to maintain the caulked portion in an optimized condition.

Furthermore, according to the present invention, it is preferable that the manufacturing method further comprises a step of applying a shot blasting to a surface of the third metallic cover beforehand.

Adopting this step surely reduces the residual tensile stress of the third metallic cover, thereby improving the stress corrosion cracking durability of the third metallic cover.

Alternatively, according to the present invention, it is preferable that the manufacturing method further comprises a step of directly welding the larger-diameter portion of the first metallic cover to the housing, after applying the shot blasting to the first metallic cover.

This step can reduce the total number of parts required for the gas sensor and can improve the airtightness and connecting strength.

Furthermore, according to the present invention, it is preferable that the manufacturing method further comprises a step of applying an oxidation treatment to the first metallic cover after applying the shot blasting to the first metallic cover.

Furthermore, according to the present invention, it is preferable that the shot blasting is performed in such a manner a compression stress is uniformly given to at least one of inner and outer surfaces of the first metallic cover. This is effective to realize a uniform removal of the residual stress.

Furthermore, according to the present invention, it is preferable that the shot blasting is applied to both of inner and outer surfaces of the first metallic cover.

Furthermore, according to the present invention, it is preferable that the shot blasting is performed so as to satisfy a relationship that B/A is equal to or larger than 0.8, where "A" represents an entire surface area of the first metallic cover and "B" represents a total area of dents formed on the surface of the first metallic cover.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Preferred embodiments of the present invention will be explained hereinafter with reference to attached drawings. Identical parts are denoted by the same reference numerals throughout the drawings. In the following description, a front or lower side of a gas sensor to be exposed to a measured gas is referred to as a distal end side and the opposite side is referred to as a proximal end side.

Gas Sensor Arrangement

A preferred arrangement of a gas sensor according to the present invention will be explained with reference to FIGS. 1 to 3.

A gas sensor 1 is an oxygen sensor used for an automotive internal combustion engine.

Figure 1:
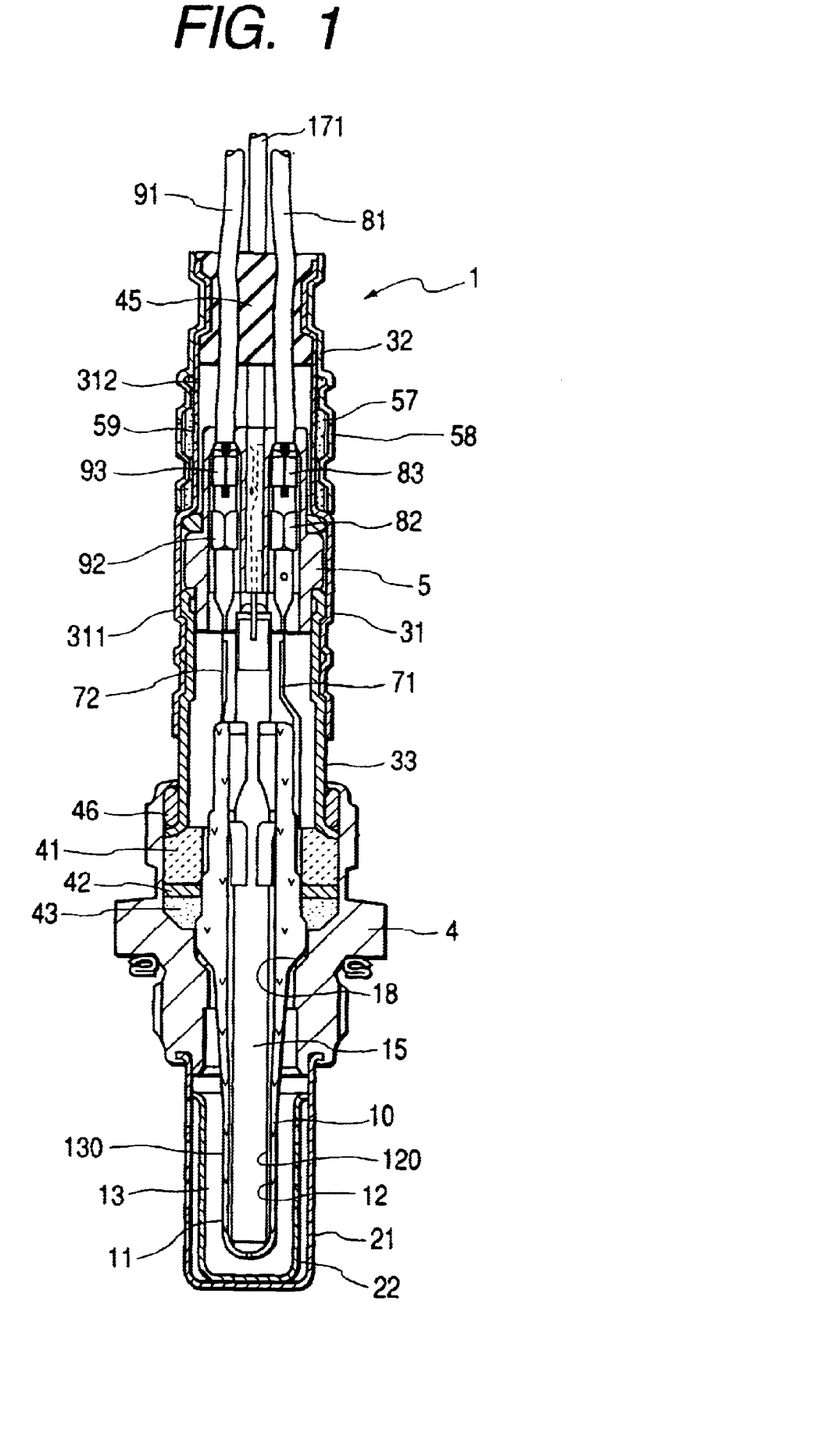
FIG. 1 is a vertical cross-sectional diagram showing a gas sensor incorporating a metallic cover in accordance with a preferred embodiment of the present invention.

As shown in FIG. 1, the gas sensor 1 comprises a sensing element 10 having a gas contact portion 11 exposed to a measured gas, a housing 4 holding the sensing element 10, protective covers 21 and 22 extending from a distal end of the housing 4 as a double-layered cover surrounding the gas contact portion 11 of the sensing element 10.

The sensing element 10 has an inside space serving as a reference gas chamber 12 into which air is introduced. A measured gas chamber 13 is provided around an outer surface of the sensing element 10 so as to surround the gas contact portion 11. A reference electrode 120 is provided on an inner surface of the sensing element 10 and a sensing electrode 130 is provided on an outer surface of the sensing element 10. Both of the reference electrode 120 and the sensing electrode 130 are made of platinum. A heater 15 is disposed in the inside space of the sensing element 10.

The sensing element 10 is connected to signal output terminals 71 and 72 which are connected via connecting terminals 82 and 92 and metallic terminals 83 and 93 to leads 81 and 91 which extend out of the gas sensor 1. The signal output terminals 71 and 72 are connected to terminals of the reference electrode 120 and the sensing electrode 130 formed on the inner and outer surfaces of the sensing element 10. A lead 171 supplies electric power to the heater 15.

Connecting portions of the leads 81 and 91 and the connecting terminals 82 and 92 are held in an insulating member 5. The insulating member 5, which is electrically non-conductive, is held in a third metallic cover 33 and a first metallic cover 31 overlapped with each other and extending successively from a proximal end of the housing 4. A proximal end of the first metallic cover 31 is overlapped via a water-repellent filter 57 with a second metallic cover 32. A proximal end of the second metallic cover 32 is opened, and an elastic insulating member 45 is disposed in this opening so as to allow the leads 171, 81 and 91 to extend out of the gas sensor 1.

As shown in FIG. 1, a distal end (i.e., a lower end) of the third metallic cover 33 is placed inward from the proximal edge (i.e., an upper edge) of the housing 4. A metallic ring 46 interposes between the third metallic cover 33 and the housing 4. Overlapped portions of the third metallic cover 33 and the housing 4 are firmly caulked via the metallic ring 46.

A proximal end (i.e., an upper end) of the third metallic cover 33 is placed inside a larger-diameter portion 311 of the first metallic cover 31. Overlapped portions of the first metallic cover 31 and the third metallic cover 33 are caulked together by applying a pressing force from outside to inside in the radial direction.

A smaller-diameter portion 312 of the first metallic cover 31 is placed inside the second metallic cover 32. Overlapped portions of the first metallic cover 31 and the second metallic cover 32 are caulked together via the water-repellent filter 57 by applying a pressing force from outside to inside in the radial direction.

The larger-diameter portion 311 is formed at a distal end side of the first metallic cover 31, and the smaller-diameter portion 312 is formed at a proximal end side of the first metallic cover 31.

The gas sensor 1 measures an electromotive force generated in the sensing element 10 in accordance with a concentration difference between an objective gas introduced in the reference gas chamber 12 and the air introduced in the measured gas chamber 13. A sensing signal representing the concentration of the objective measured gas is taken out of the gas sensor 1 via the leads 81 and 91.

The second metallic cover 32 has a first air hole 58, and the smaller-diameter portion 312 of the first metallic cover 31 has a second air hole 59. The water-repellent filter 57 interposes between the first air hole 58 and the second air hole 59 so that the air is introduced into the reference gas chamber 12 of the sensing element 10 via the water-repellent filter 57.

A sealing member 43, a pad 42, an insulating member 41, and a packing 18 are placed in the inside space of the housing 4 to accommodate the sensing element 10 at an appropriate position. The sensing element 10 partly protrudes from the distal end (i.e., a lower end) of the housing 4 and is covered by the protective covers 21 and 22.

The sensing element 10 of this embodiment has a cup-shaped solid electrolytic body in which the heater 15 is placed. The inside space of the sensing element 10 is the reference gas chamber 12, and the outside of the sensing element 10 is the measured gas chamber 13.

In the manufacturing of the above-described gas sensor 1, the first metallic cover 31, the second metallic cover 32, the third metallic cover 33, and other components are manufactured separately and are later assembled integrally. Especially, according to this embodiment, after the first metallic cover 31 is configured into a predetermined shape, the shot blasting is applied to the surface of the first metallic cover 31.

Manufacturing Method

Hereinafter, a manufacturing method of the first metallic cover 31 is explained in more detail.

Figure 2A:
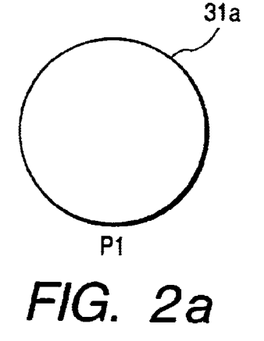
FIGS. 2a–2e show a flow diagram showing a first press shaping work for the metallic cover according to a manufacturing method of the preferred embodiment of the present invention.
Figure 2B:
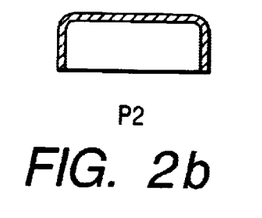
Figure 2C:
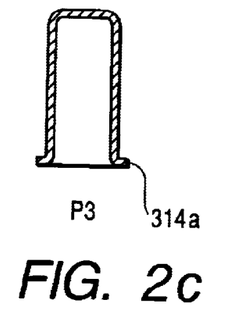
Figure 2D:
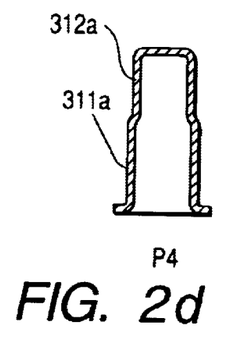
Figure 2E:
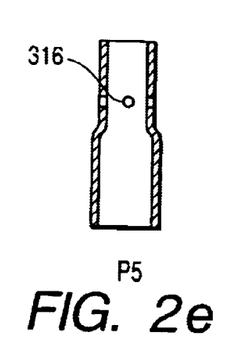
Figure 3A:
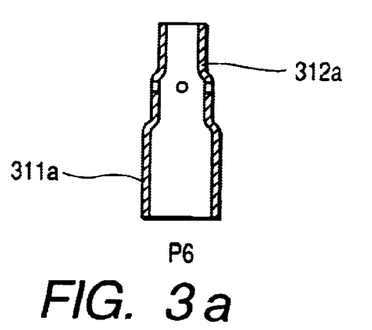
FIGS. 3a–3b show a flow diagram showing a second press shaping work according to the manufacturing method of the preferred embodiment of the present invention.
Figure 3B:
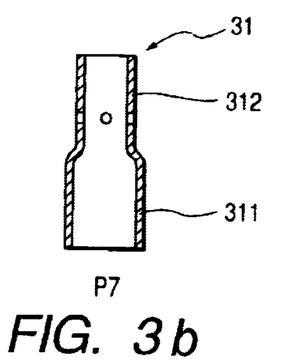

The first metallic cover 31 of this embodiment is formed by press working a plate or tubular material 31a made of SUS304L as shown in FIGS. 2 and 3.

First, in a step P1 of FIG. 2a, a blank of the plate or tubular material 31a is prepared. Then, in steps P2 and P3 of FIGS. 2b and 2c, the plate or tubular material 31a is successively configured through the press drawing into a cup-shaped member having a smaller diameter and elongated in the axial direction. In the next step P4 of FIG. 2d, the cup-shaped member is further deformed into a stepped shape through the drawing to have a larger-diameter portion 311a and a smaller-diameter portion 312a, thereby accomplishing a first press shaping work.

Next, in step P5 of FIG. 2e, the bottom the cup-shaped member, i.e., a closed end of the smaller-diameter portion 312a is removed off by cutting. A lateral hole 316 is opened on a side wall of the smaller-diameter portion 312a. Then, a flange portion 314a, i.e., an open end of the larger-diameter portion 311a, is removed off by trimming, thereby obtaining a semi-finished product of the first metallic cover 31.

Next, the semi-finished product of the first metallic cover 31 is subjected to a cleaning process according to which the semi-finished product is soaked in alkali cleaning fluid of for example 50° C. to 60° C. Then, the product is subjected to an annealing process according to which the product is heated in a vacuum furnace at a high temperature of for example 1,050° C. for several tens minutes and subsequently cooled down in the atmosphere of $N_2$ gas.

Next, in step P6 of FIG. 3a, a second press shaping work is performed to squeeze the edge of the smaller-diameter portion 312a. Then, in step P7 of FIG. 3b, the squeezed edge of the smaller-diameter portion 312a is expanded to form the smaller-diameter portion 312 having a required size of this embodiment, thereby accomplishing the formation of the first metallic cover 31. At this moment, hardness of the smaller-diameter portion 312 is higher than that of the larger-diameter portion 311 due to the second press shaping work applied only to the smaller-diameter portion 312 after finishing the annealing process.

In general, when two overlapped metallic tubes are caulked, it is preferable that the inner metallic tube has a hardness higher than that of the outer tube.

According to this embodiment, the smaller-diameter portion 312 of the first metallic cover 31 is positioned inside the second metallic cover 32 when caulked together. In this respect, the smaller-diameter portion 312 of the first metallic cover 31 should have a higher hardness compared with that of the second metallic cover 32. On the other hand, the larger-diameter portion 311 of the first metallic cover 31 is positioned outside the third metallic cover 33 when caulked together. Accordingly, the larger-diameter portion 311 of the first metallic cover 31 should have a lower hardness compared with that of the third metallic cover 33.

In view of the above, the second press shaping work is performed in such a manner that the hardness of the smaller-diameter portion 312 becomes higher than that of the larger-diameter portion 311.

Next, according to this embodiment, the shot blast processing is applied to the surface of the first metallic cover 31 thus fabricated.

The shot blast processing is performed to clean and descale the first metallic cover 31 by means of a stream of abrasive powder, such as glass beads having a particle size in the range from 90 $\mu$m to 63 $\mu$m, blown through a nozzle under air pressure of 4.5 Kg/cm$^2$. A required processing time for the shot blasting is approximately 10 minutes. Details of the shot blast processing will be explained later with reference to FIGS. 9 and 10.

By applying the shot blast processing, fabrication of the first metallic cover 31 is accomplished. Although application of the shot blast processing slightly increases the surface hardness of the first metallic cover 31, the hardness relationship between the smaller-diameter portion 312 and the larger-diameter portion 311 remains unchanged. The hardness of the inner surface of first metallic cover 31 is also not changed before and after the shot blast processing.

According to this embodiment, after finishing the shot blast processing, the first metallic cover 31 is subjected to an oxidation treatment for oxidizing the surface of the first metallic cover 31. More specifically, the first metallic cover 31 is held in the air at 500° C. for 20 minutes to oxidize the surface of the first metallic cover 31. This oxidation treatment effectively prevents the first metallic cover 31 from being progressively oxidized during the operation of the gas sensor 1. As a result, measuring accuracy of the gas sensor can be improved.

Each of the second metallic cover 32 and the third metallic cover 33 is fabricated separately. The shot blasting is applied to the surfaces of the second metallic cover 32 and the third metallic cover 33 thus fabricated.

In an assembling process, the second metallic cover 32 is overlapped on an outer surface of the smaller-diameter portion 312 of the first metallic cover 31. Then, overlapped portions of the first metallic cover 31 and the second metallic cover 32 are firmly fixed together by caulking. Furthermore, the larger-diameter portion 311 of the first metallic cover 31 is overlapped on an outer surface of the third metallic cover 33. Then, overlapped portions of the first metallic cover 31 and the third metallic cover 33 are firmly fixed together by caulking.

Function and Effect

Next, function and effect of this embodiment will be explained.

According to this embodiment, the first metallic cover 31 is subjected to the shot blast processing after being configured into a predetermined shape. Hence, it becomes possible to reduce the surficial residual tensile stress while maintaining improved mechanical properties of the first metallic cover 31 obtained through the press shaping work. Accordingly, it becomes possible to suppress the tensile residual stress even after the first metallic cover 31 is connected with the second metallic cover 32 and the third metallic cover 33. It becomes possible to greatly improve the stress corrosion cracking durability of the metallic cover.

Evaluation Test

To evaluate the manufacturing method of the above-described embodiment in comparison with a conventional method, a durability test with respect to stress corrosion cracking properties of the first metallic cover was conducted for the gas sensors according to the present invention and gas sensors according to the prior art.

Prepared samples include a total of five kinds of gas sensors according to the present invention (i.e., samples E11 to E14 and E2) as well as a total of four kinds of conventional gas sensors (i.e., samples C1 to C4).

Sample E11 comprises a fist metallic cover which is manufactured according to the manufacturing method of the present invention but is not subjected to the aging processing (i.e., surface oxidation treatment).

Each of samples E12 and E14 comprises a first metallic cover which is manufactured according to the manufacturing method of the present invention and is subjected to the aging processing for 20 minutes at the temperature of 400° C. (E12), 500° C. (E13), or 600° C. (E14).

Sample C1 comprises a first metallic cover which is manufactured according to a conventional manufacturing method including three extra processes in addition to the processes of the above-described preferred embodiment. Sample C1 is not subjected to the shot blast processing.

Each of samples C2 to C4 comprises a fist metallic cover which is manufactured according to the same conventional manufacturing method applied to sample C1 and is subjected to the aging processing for 20 minutes at the temperature of 400° C. (C2), 500° C. (C3), or 600° C. (C4).

Sample E2 comprises a first metallic cover which is manufactured according to the manufacturing method of the present invention except for the annealing process.

All of the samples E11 to E14 and E2 are subjected to the shot blast processing of the present invention.

A stress corrosion cracking test was conducted for all of the nine samples E11–E14, E2, and C1–C4. First, the boiling point of a test solution was adjusted to 143° C. by using magnesium oxide (MgCl$_2$) reagent and distilled water. The concentration of the test solution was approximately 42%. The first metallic cover was soaked in this test solution for 2 hours. After that, presence of cracks appearing on the surface of the first metallic cover was observed.

Figure 4:
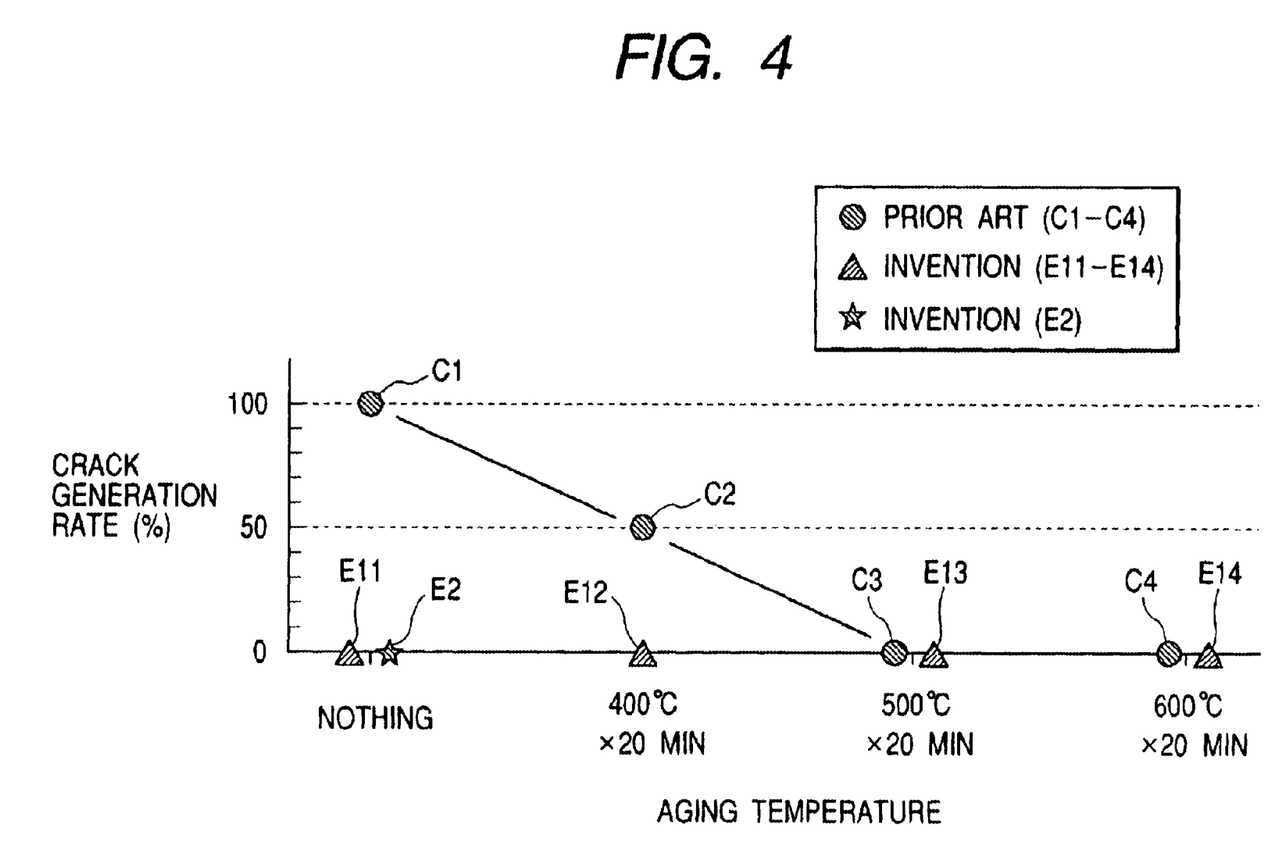
FIG. 4 is a graph showing the result of a stress corrosion cracking test in accordance with the preferred embodiment of the present invention.

FIG. 4 shows the result of the stress corrosion cracking test, in which an abscissa represents an aging temperature and an ordinate represents a crack generation rate (%).

As understood from FIG. 4, the conventional gas sensors could not suppress generation of cracks without performing the aging processing. According to the conventional method, the aging temperature must be increased up to 500° C. to surely suppress generation of cracks.

On the other hand, all of the tested samples according to the present invention demonstrated satisfactory durability regardless of adoption of the aging processing. This is believed as an effect brought by the shot blast processing applied according to the present invention.

Furthermore, according to the result of the sample E2, it was confirmed that satisfactory durability can be assured even if the annealing processing is omitted. This makes it possible to reduce the total number of manufacturing processes.

Modified Metallic Cover (I)

Figure 5:
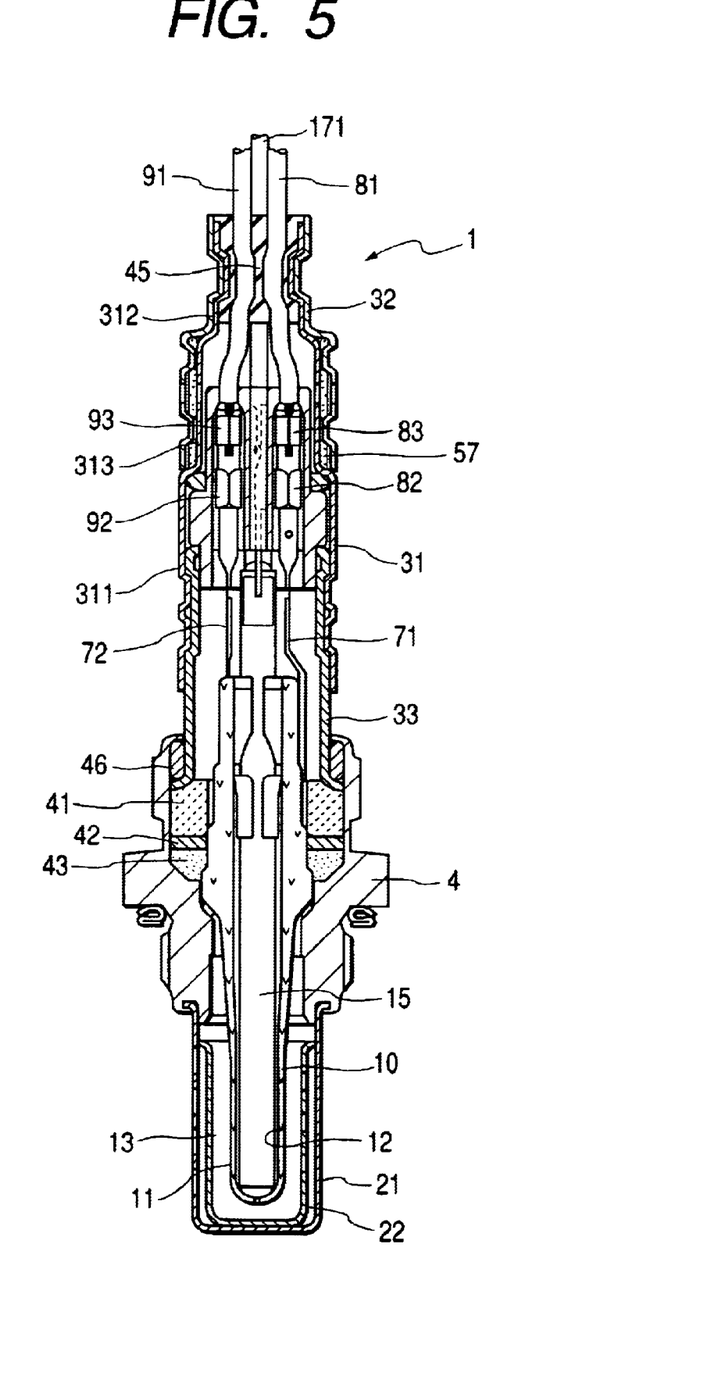
FIG. 5 is a vertical cross-sectional diagram showing a gas sensor incorporating a modified metallic cover in accordance with the preferred embodiment of the present invention.
Figure 6:
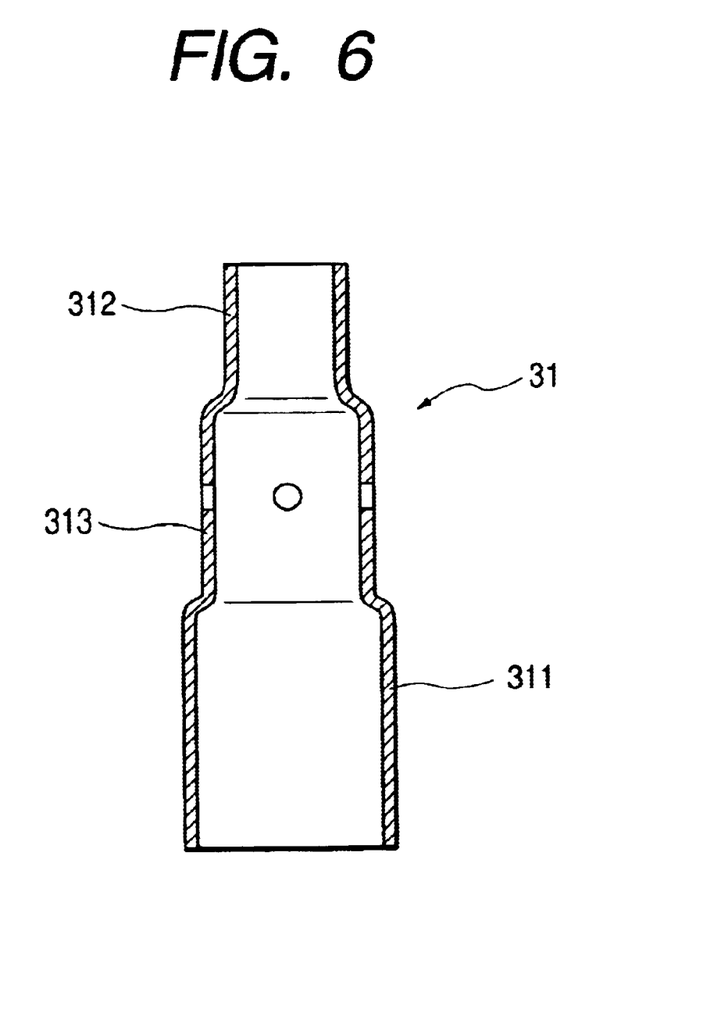
FIG. 6 is a vertical cross-sectional diagram showing the modified metallic cover shown in FIG. 5.

FIGS. 5 and 6 show a modified gas sensor in accordance with the present invention which is different in that the configuration of first metallic cover 31 is modified.

For the gas sensor 1 shown in FIG. 5, the first metallic cover 31 is manufactured into a three-stepped shape (refer to FIG. 6) having an intermediate portion 313 between the larger-diameter portion 311 and the smaller-diameter portion 312. The intermediate portion 313 has a diameter smaller than that of the larger-diameter portion 311 and larger than that of the smaller-diameter portion 312.

To manufacture the first metallic cover 31 shown in FIG. 6, the above-described second press shaping step P7 needs to be modified in such a manner that expansion of the squeezed edge of the smaller-diameter portion 312a is restricted to a certain amount to leave the three-stepped shape of the first metallic cover 31 shows in FIG. 6. Other manufacturing processes are basically identical with those of the above-described embodiment.

Modified Metallic Cover (II)

Figure 7:
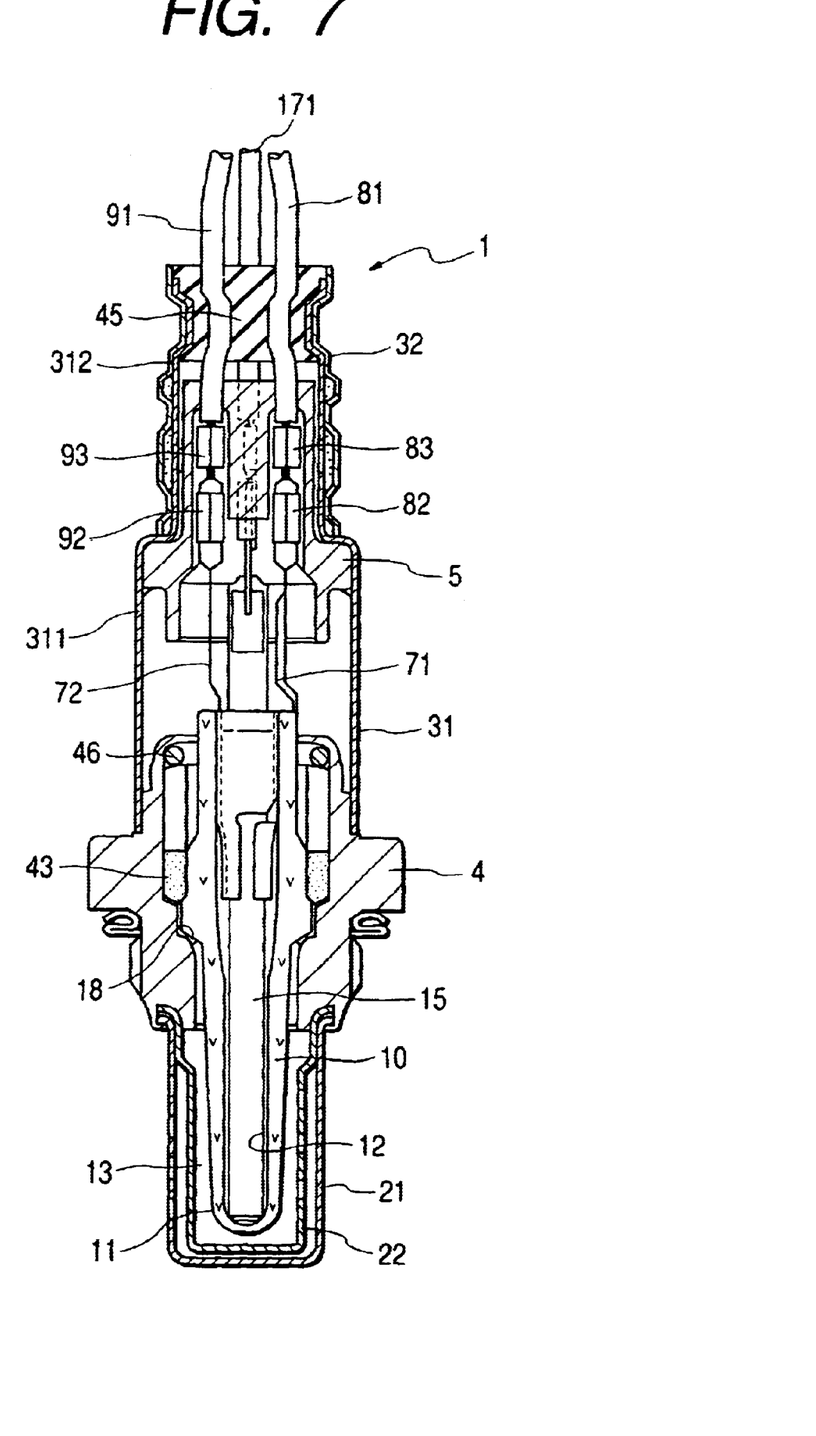
FIG. 7 is a vertical cross-sectional diagram showing a gas sensor incorporating another modified metallic cover in accordance with the preferred embodiment of the present invention.
Figure 8:
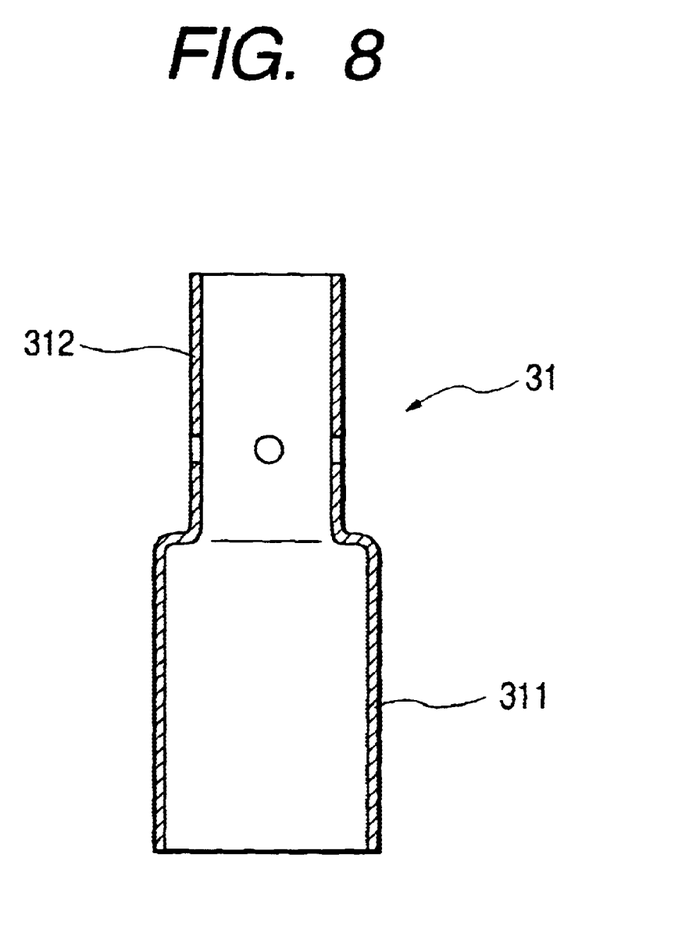
FIG. 8 is a vertical cross-sectional diagram showing the modified metallic cover shown in FIG. 7.

FIGS. 7 and 8 show another modified gas sensor in accordance with the present invention which is different in that the third metallic cover 33 is omitted and the configurations of the insulating member 5 and the first metallic cover 31 are modified.

The larger-diameter portion of the first metallic cover 31 is directly welded to the housing 4.

According to this modification, the manufacturing processes can be simplified due to omission of the third metallic cover 33 and reshaping of the insulating member 5 and the first metallic cover 33.

Shot Blast Processing

Figure 9:
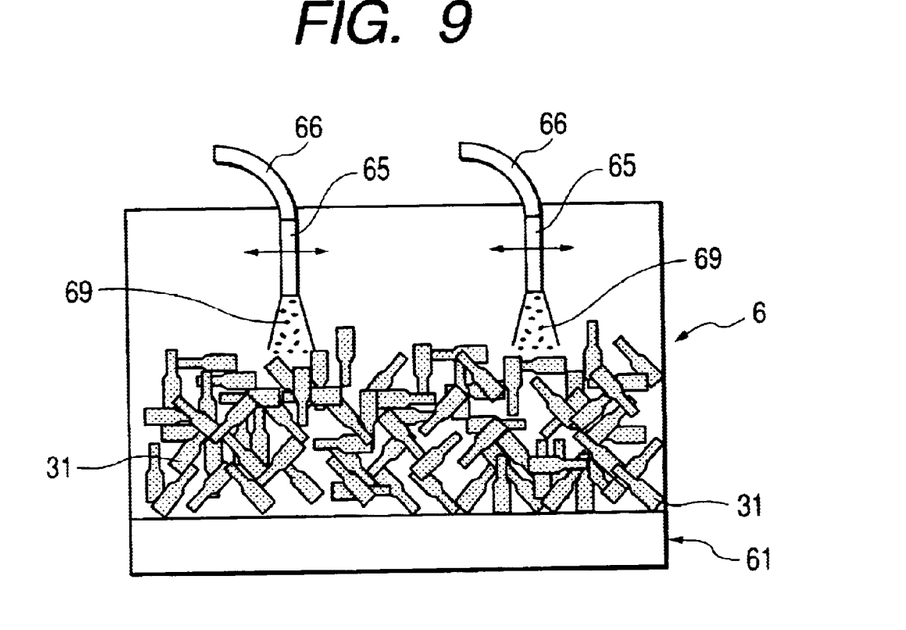
FIG. 9 is a front view showing a shot blasting apparatus in accordance with the preferred embodiment of the present invention.
Figure 10:
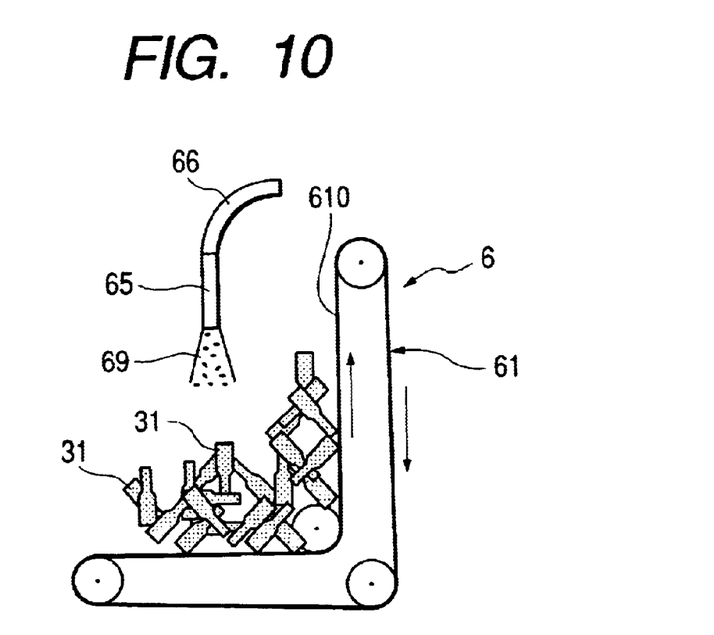
FIG. 10 is a side view showing the shot blasting apparatus in accordance with the preferred embodiment of the present invention.

FIGS. 9 and 10 show a shot blasting apparatus 6 in accordance with the preferred embodiment of the present invention which can process a lot of semi-finished products of the first metallic cover 31 at a time.

The shot blasting apparatus 6 comprises a belt conveyor 61 conveying numerous semi-finished products of the first metallic cover 31. In FIG. 10, the belt conveyor 61 has an endless belt 610 disposed in an L shape via pulleys. Each semi-finished product of the first metallic cover 31 is propelled by the belt 610 rotating in the direction shown by the arrow in FIG. 10. More specifically, each semi-finished product of the first metallic cover 31 is shifted right when positioned on a horizontal plane of the belt 610 and then raised upward when faced or abutted to a vertical plane of the belt 610, and subsequently drops or returns to the horizontal plane of the belt 610 due to free fall. In this manner, each semi-finished product of the first metallic cover 31 is moved cyclically along substantially a right triangular path while it rotates arbitrarily about its axis.

Furthermore, two sets of nozzles 65 each having an injection port directed downward are installed above the belt conveyor 61. Each nozzle 65 injects small shot blasting balls 69 together with compressed air of 4.5 Kg/cm$^2$ through a piping 66. As indicated by the arrow in FIG. 9, each nozzle 65 continuously reciprocates in a horizontal direction so that the shot blasting balls 69 can be uniformly blown on the first metallic covers 31 on the belt 610. The shot blasting balls 69 are glass beads having a particle size in the range from 90 $\mu$m to 63 $\mu$m.

According to the shot blasting apparatus 6 of this embodiment, each of first metallic covers 31 is moved along the substantially right triangular path while it rotates arbitrarily about its axis in accordance with the shift movement of the belt 610. The shot blasting is continuously repeated for an appropriate period of time so that the shot blast balls 69 uniformly hit the outer and inner surfaces of each metallic cover 31.

Through this shot blast processing, an appropriate compression stress is given to both of the outer and inner surfaces of the first metallic cover 31 so as to relax or cancel the residual tensile stress.

If the shot blasting time is too short, an applied compression stress will be insufficient. The residual tensile stress will not be removed sufficiently. On the other hand, if the shot blasting time is too long, the first metallic cover 31 may deform undesirably. An optimum time for the shot blasting processing can be obtained through experimental tests.

Next, influence of the shot blast processing given to the stress corrosion cracking durability was checked in various coverage values of the shot blasting. The shot blast coverage is variable depending on the processing conditions as well as the processing time.

More specifically, the shot blasting balls 69 leave numerous dents on the surface of the first metallic cover 31. The shot blast coverage is defined as a ratio of a total area "B" of the dents relative to an entire surface area "A" of the first metallic cover 31.

The stress corrosion cracking durability was tested on a total of three samples which were classified into 50%, 80% and 100% with respect to the shot blast coverage ($=(B/A)\times 100\%$).

Figure 11:
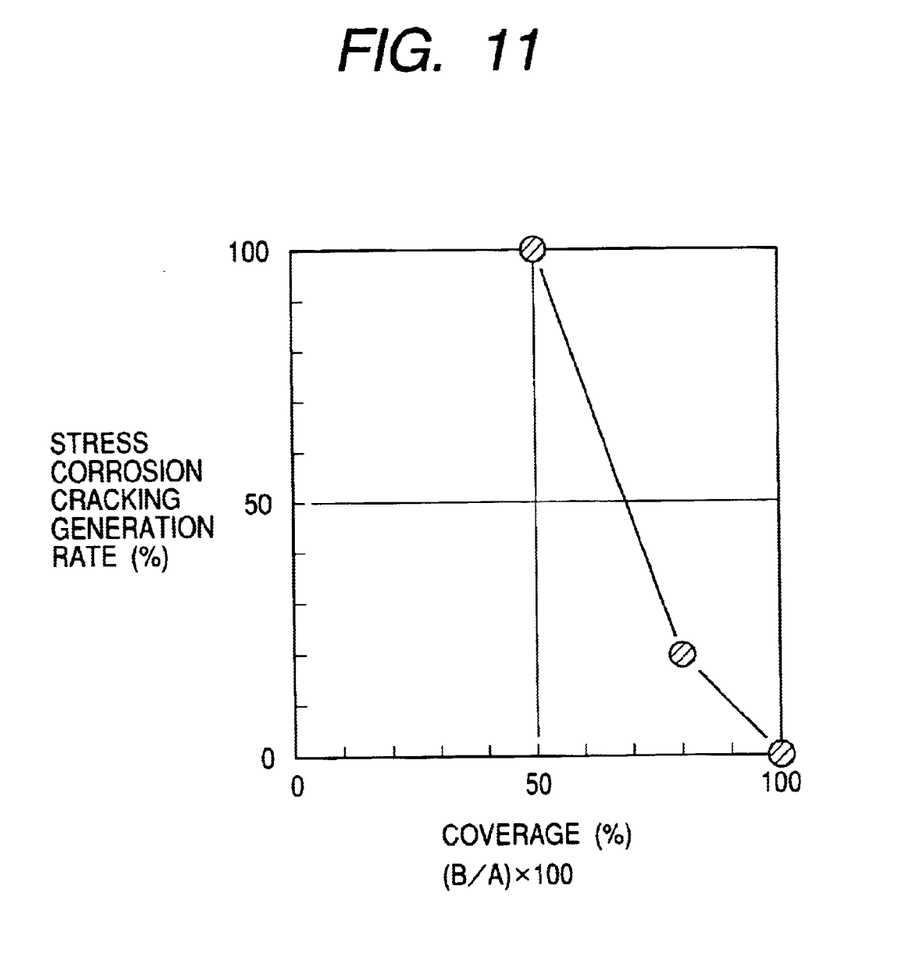
FIG. 11 is a graph showing a relationship between a shot blast coverage and a stress corrosion cracking generation rate in accordance with the preferred embodiment of the present invention.

FIG. 11 shows the result of the stress corrosion cracking test, in which an abscissa represents the shot blast coverage ($=(B/A)\times 100(\%)$) and an ordinate represents a crack generation rate (%).

As understood from FIG. 11, when the shot blast coverage is equal to or larger than 80%, the crack generation rate can be suppressed to 20% or less. On the other hand, when the shot blast coverage is equal to or less than 50%, the crack generation rate reaches 100%.

The manufacturing method of the present invention is not limited to an oxygen sensor and therefore can be applied to various gas sensors, such as a NOx sensor, a $CO_2$ sensor or the like.

Furthermore, according to the present invention, the cup-shaped solid electrolytic body can be replaced with a plate or flat sensing element.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A method for manufacturing a gas sensor comprising a sensing element having a gas contact portion exposed to a measured gas, a housing holding said sensing element, a protective cover extending from a distal end of said housing and surrounding said gas contact portion of said sensing element, and a first metallic cover surrounding signal output terminals and leads connected to said sensing element, said manufacturing method comprising the steps of:

forming a semi-finished product of said first metallic cover;

applying a shot blasting to a surface of said semi-finished product of said first metallic cover; and after said step of shot blasting, assemblying said first metallic cover with said sensing element, said housing, and said protecting cover to produce a gas sensor.

2. The manufacturing method in accordance with claim 1, wherein said semi-finished product of said first metallic cover is configured into a predetermined shape having a larger-diameter portion positioned near said housing and a smaller-diameter portion positioned far from said housing, before applying the shot blasting to said first metallic cover.

3. The manufacturing method in accordance with claim 2, wherein said smaller-diameter portion has a hardness higher than that of said larger-diameter portion when said semi-finished product of said first metallic cover is formed.

4. The manufacturing method in accordance with claim 3, wherein said semi-finished product of said first metallic cover is formed through the steps of: configuring a plate or tubular material into a predetermined shape having said larger-diameter portion;

subjecting the shaped material to a thermal treatment; and reshaping part of the thermally treated material to form said smaller-diameter portion.

5. The manufacturing method in accordance with claim 4, further comprising, after said configuring step, subjecting the shaped material to a cleaning process according to which the semi-finished product is soaked in alkali cleaning fluid.

6. The manufacturing method in accordance with claim 4, wherein said thermal treatment comprises an annealing process according to which the semi-finished product is heated in a vacuum furnace at a high temperature of about 1050° C. and subsequently cooled in an atmosphere of $N_2$ gas.

7. The manufacturing method in accordance with claim 2, further comprising the steps of:

overlapping a second metallic cover on an outer surface of said smaller-diameter portion of said first metallic cover; and caulking overlapped portions of said second metallic cover and said smaller-diameter portion of said first metallic cover.

8. The manufacturing method in accordance with claim 7, further comprising a step of applying a shot blasting to a surface of said second metallic cover before said overlapping step.

9. The manufacturing method in accordance with claim 2, further comprising the steps of:

overlapping said larger-diameter portion of said first metallic cover on an outer surface of a third metallic cover at one end thereof after applying the shot blasting to said first metallic cover, while connecting the other end of said third metallic cover to said housing; and caulking overlapped portions of said third metallic cover and said larger-diameter portion of said first metallic cover.

10. The manufacturing method in accordance with claim 9, further comprising a step of applying a shot blasting to a surface of said third metallic cover before said overlapping step.

11. The manufacturing method in accordance with claim 2, further comprising a step of:

directly welding said larger-diameter portion of said first metallic cover to said housing, after applying the shot blasting to said first metallic cover.

12. The manufacturing method in accordance with claim 1, further comprising a step of applying an oxidation treatment to said first metallic cover after applying the shot blasting to said first metallic cover.

13. The manufacturing method in accordance with claim 12, wherein said oxidation treatment comprises holding said first metallic cover in air at a temperature of 500° C.–600° C. to oxidize the surface of the first metallic cover.

14. The manufacturing method in accordance with claim 1, wherein said shot blasting is performed in such a manner that a compression stress is uniformly given to at least one of inner and outer surfaces of said first metallic cover.

15. The manufacturing method in accordance with claim 1, wherein said shot blasting is applied to both of inner and outer surfaces of said first metallic cover.

16. The manufacturing method in accordance with claim 1, wherein said shot blasting is performed so as to satisfy a relationship that B/A is equal to or larger than 0.8, where "A" represents an entire surface area of said first metallic cover and "B" represents a total area of dents formed on the surface of said first metallic cover.

17. The manufacturing method in accordance with claim 1, wherein said step of applying a shot blasting comprises directing a stream of particles against said surface of said semi-finished first metallic member.

18. The manufacturing method in accordance with claim 17, wherein said particles comprise glass beads blown through a nozzle under air pressure.

19. The manufacturing method in accordance with claim 18, wherein said glass beads have a particle size in a range from 90 $\mu$m to 63 $\mu$m.

20. The manufacturing method in accordance with claim 1, wherein the hot blasting is restricted to only the surficial layer so that an inner layer of the semi-finished first metallic cover is free from influence of the shot blasting.

* * * * *